United States Patent
Abdel-Rahman

(10) Patent No.: US 6,593,567 B1
(45) Date of Patent: Jul. 15, 2003

(54) ION MOBILITY SPECTROMETER HAVING EXTENDED LINEAR DYNAMIC RANGE

(75) Inventor: Mahmoud F. Abdel-Rahman, Newark, DE (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/567,811

(22) Filed: May 9, 2000

(51) Int. Cl.[7] ............................................. G01N 27/62

(52) U.S. Cl. ..................... 250/286; 250/287; 250/292; 250/315.3; 324/457; 324/464; 324/458; 324/750; 324/71.1

(58) Field of Search ............................. 250/286, 287, 250/292, 370.07, 208.1, 315.3; 324/457, 464, 458, 750, 123 R, 71.1

(56) References Cited

U.S. PATENT DOCUMENTS

| | | | | |
|---|---|---|---|---|
| 5,047,723 | A | * | 9/1991 | Puumalainen ............... 250/287 |
| 6,100,698 | A | * | 8/2000 | Megerle et al. ............. 250/286 |
| 6,124,592 | A | * | 9/2000 | Spangler ..................... 250/287 |
| 6,353,324 | B1 | * | 3/2002 | Uber et al. .................. 324/457 |

OTHER PUBLICATIONS

R. H. Hill and D. G. McMinn, *Detectors for Capillary Chromatography*, pp. 311–313 (John Wiley & Sons, Inc., 1992).

* cited by examiner

Primary Examiner—John R. Lee
Assistant Examiner—Zia R. Hashmi

(57) ABSTRACT

An ion mobility spectrometer is disclosed which includes a sample input port, an ion generator, an ionization chamber receiving and ionizing samples, an ion gate for causing the ionized samples to travel in a direction, and a drift region for receiving the directed ionized samples and for subjecting the ionized samples to an electric potential. The ionized samples then separate according to their electric charge and mass and are detected by a sensor having an output with linear, non-linear, and logarithmic characteristics. The ion mobility spectrometer further includes circuitry coupled to the sensor for linearizing the output such that the non-linear and logarithmic characteristics are linearized while preserving the linear characteristics. The circuitry operates to linearize the output by multiplying the output by a first function determined from a second function by extrapolating linear and logarithmic characteristics based on a logarithmic plot, dividing the output current by the extrapolation, adding 1, and raising the result to a power determined from a slope of the logarithmic characteristics to obtain a linearizing function. The result is one continuous linear plot in conformance with the fundamental gain of the IMS detector.

12 Claims, 5 Drawing Sheets

ION MOBILITY SPECTROMETER HAVING EXTENDED LINEAR DYNAMIC RANGE

FIELD OF THE INVENTION

This invention relates to spectrometers, in particular to spectrometers for detecting ions based on their mobility.

BACKGROUND OF THE INVENTION

An ion mobility spectrometer (IMS, also referred to as an ion mobility detector) is a chemical detector whose operation is based on the fact that different ions have different electric charges and masses. As a result, when moving in a reference gas in an electric field, the different ions have different mobility, or velocity, as a result of the electric field. An IMS typically includes an ion source for generating ions, an ionization chamber where ion-molecule reactions occur as a result of samples being bombarded with the generated ions, an ion gate region for directing the ionized samples, also referred to as secondary ions, to be analyzed, an ion drift region to allow the ionized samples to separate so that they may be detected, and an ion collection region for detection and identification of the sample ions. In the ionizer, radioactive materials such as, for example, tritium, Ni, Am, etc. may be used to ionize the samples. An electric field is typically used in the ion gate region to direct the ions into the ion drift region. In the ion drift region, the sample ions are again subjected to an electric field where they separate according to their mobility, as mentioned above.

Unlike a mass spectrometer, which requires a high vacuum, the IMS has the advantage of operating under atmospheric pressure. It can be used as a stand-alone detector using its own analyte separating ability. It also can be used in combination with other analytical techniques. For example, an IMS can be used as a chromatographic detector where analyte separation first takes place in a column mounted upstream of the IMS. The resulting separated output is then directed into an IMS for further analysis. This multiple analysis technique has been used successfully in Gas Chromatography, Liquid Chromatography and Super-Critical Chromatography.

The IMS is a highly sensitive detector with detection limits observed well below ranges in nanograms. However the IMS suffers from a limited dynamic range due to a response decay at higher analyte concentrations. Like other concentration-dependent ionization detectors, the IMS is linear only up to a limit determined primarily by the strength of the ionization source. It is estimated that this limit may be reached when half the ionizing particles are consumed in ionizing analyte molecules. After the limit of the linear response of the IMS, there is a transitional range where the response becomes non-linear. Eventually, at high sample concentrations, the IMS response becomes logarithmic in nature. It is known to use a logarithmic calibration curve to compensate for this logarithmic response.

Reference in this regard may be had to R. H. Hill and D. G. McMinn, "Detectors for Capillary Chromatography," pp. 311–313 (John Wiley & Sons, Inc., 1992)

A disadvantage of the IMS is that the user must often dilute samples in order to work within the linear range.

Another disadvantage is that in the event that the user wishes to use high sample concentrations without dilution, the user must determine the beginning of the logarithmic range independently, as there are no currently available guidelines, and then establish a logarithmic calibration curve specifically for the particular analytes of interest.

An additional disadvantage is that the above mentioned transitional range between the linear range and the logarithmic range is typically not calibrated. Therefore, determining concentrations of analytes falling in this region requires a complex calibration curve.

OBJECTS AND ADVANTAGES OF THE INVENTION

It is an object and advantage of the invention to provide an ion mobility spectrometer which has a linear response over substantially all of its response curve. It is a further object and advantage of the invention to linearize the output of the IMS in a manner that preserves the linear response range, while linearizing the transitional response range and the logarithmic response range of the IMS response curve, thus relieving the user of complex and tedious calibration procedures.

SUMMARY OF THE INVENTION

An ion mobility spectrometer is disclosed which includes a sample input port, an ion generator, an ionization chamber receiving and ionizing samples, an ion gate for causing the ionized samples to travel in a direction, and a drift region for receiving the directed ionized samples and for subjecting the ionized samples to an electric potential. The ionized samples then separate according to their electric charge and mass and are detected by a sensor having an output with linear, non-linear, and logarithmic characteristics. The ion mobility spectrometer further includes circuitry coupled to the sensor for linearizing the output such that the non-linear and logarithmic characteristics are linearized while preserving the linear characteristics. The circuitry operates to linearize the output by multiplying the output by a first function determined from a second function by extrapolating linear and logarithmic characteristics based on a logarithmic plot, dividing the output current by the extrapolation, adding 1, and raising the result to a power determined from a slope of the logarithmic characteristics to obtain a linearizing function. The result is one continuous linear plot in conformance with the fundamental gain of the IMS detector.

PREFERRED EMBODIMENTS OF THE INVENTION

Figure 1:
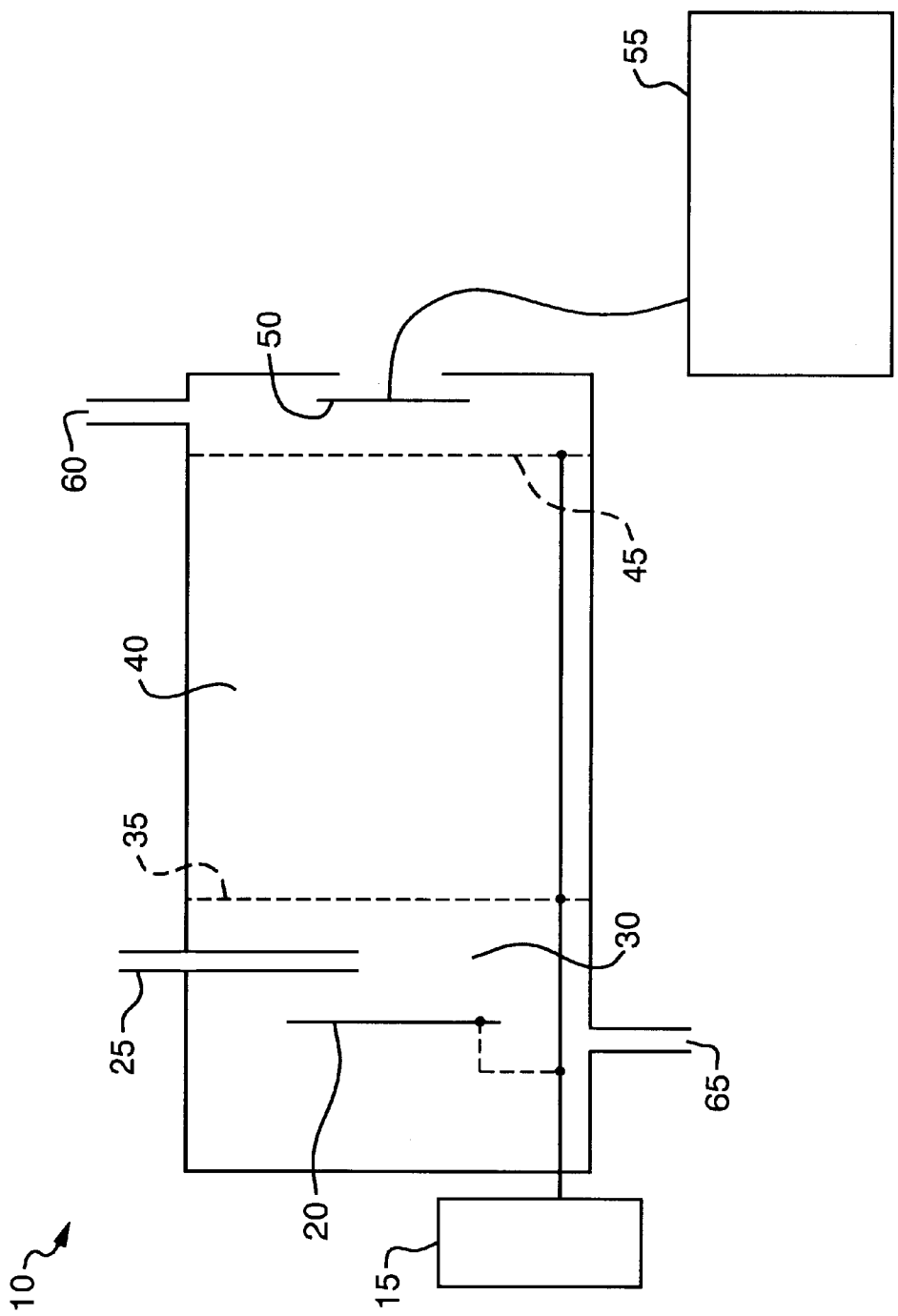
FIG. 1 shows a schematic diagram of an ion mobility spectrometer in accordance with the teachings of this invention.

FIG. 1 shows a schematic diagram of an ion mobility spectrometer 10. A power supply 15 provides power to an ion source 20, if required, and also provides voltage for establishing the electric fields, as required.

The ion source may include radioactive materials such as, for example, tritium, Ni, Am, etc., that might not require power for operation, or may include a non-radioactive source, such as a photo-ionization source which may require power.

A sample introduction port 25 introduces an analyte to be ionized into an ionization chamber 30. An ion gate 35 has an electric potential such that ions are directed into a drift region 40.

In the drift region 40, the ions are subjected to an electric field where they separate according to their mobility.

An exit gate 45 has an electric potential such that the separated ions are directed toward an ion sensor 50.

The electric field of the drift region 40 is a result of the difference in potential between the ion gate 35 and the exit gate 45. The difference in potential between the ion gate 35 and the exit gate 45 may be such that it generates an electric field, for example, in the range of 200–300 volts/cm DC. The polarity of the electric field may be such that positive ions are directed toward the ion sensor 50, or may be reversed, such that negative ions are directed toward the ion sensor 50.

The ion sensor 50 is coupled to circuitry 55 for measuring the number of ions colliding with the ion sensor 50 over time and providing a corresponding output current. The circuitry 55 is further capable of linearizing the output current in accordance with the teachings herein. The circuitry 55 may include a computing device such as a personal computer or any device capable of executing the linearization algorithm in accordance with this invention. Ports 60 and 65 provide an inlet and outlet, respectively, for a reference drift gas.

It has been observed that when the IMS detector response is in transition from the linear response range to the logarithmic response range, the transition occurs smoothly, that is, the transition occurs in a predictable fashion, without significant excursions. As a result, it is possible to devise a single function that incorporates the linearization of the transitional range together with the linearization of the logarithmic range. It has also been observed that if such a linearizing function is applied directly to the ion sensor 50 output current as it is generated (vis-a0-vis the chromatographic peak areas or heights as is the case for calibration curves), the same function with the same parameters could apply to different analytes. The reason is that the output current is the only true indication of how many of the ionization particles are consumed in analyte ionization which, as previously mentioned, is a major contributing factor to the IMS non-linearity.

Figure 2:
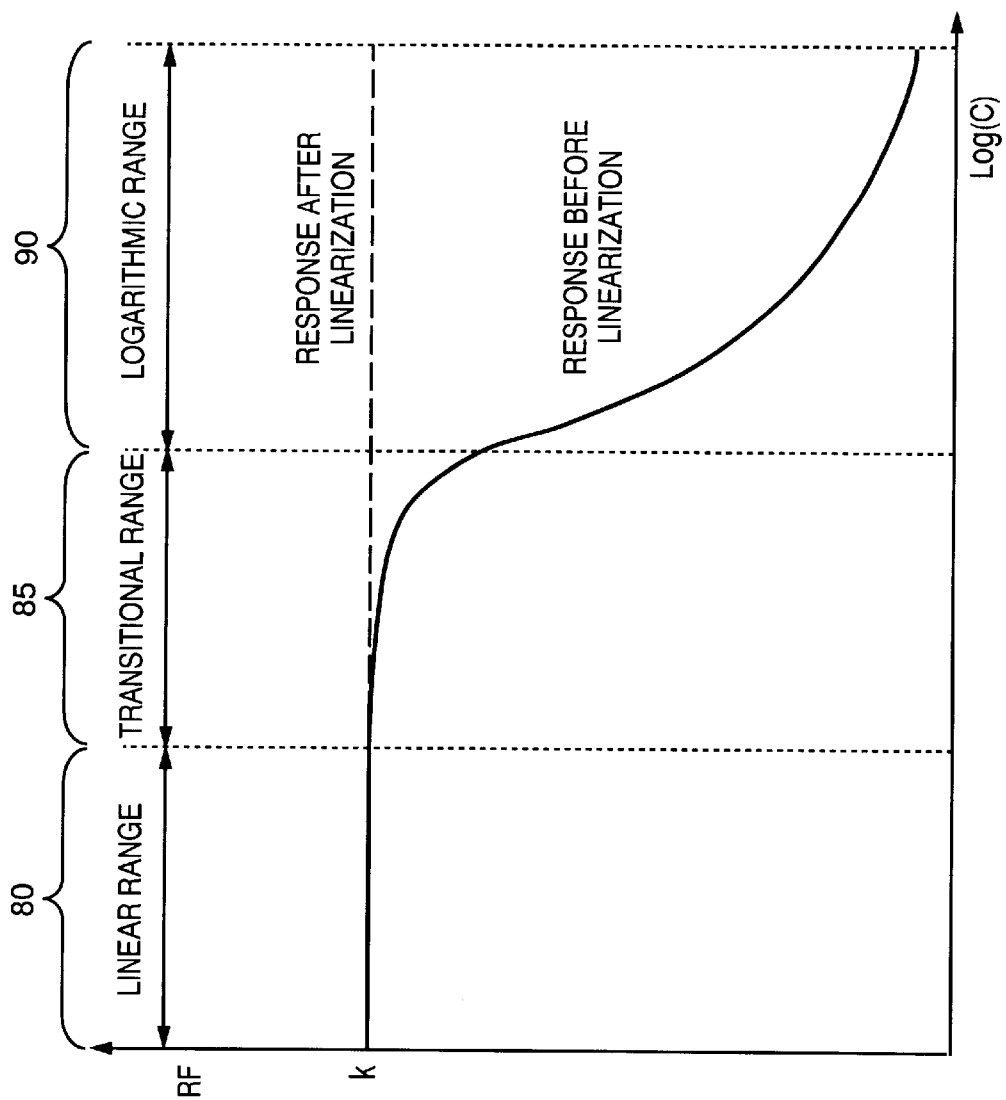
FIG. 2 shows a plot of the IMS response factor before and after linearization.

FIG. 2 is a plot of a typical IMS response factor (RF), that is, the IMS detector response per unit analyte concentration. FIG. 2 depicts the linear response range 80, the transitional response range 85, and the logarithmic response range 90 both before and after linearization.

Figure 3:
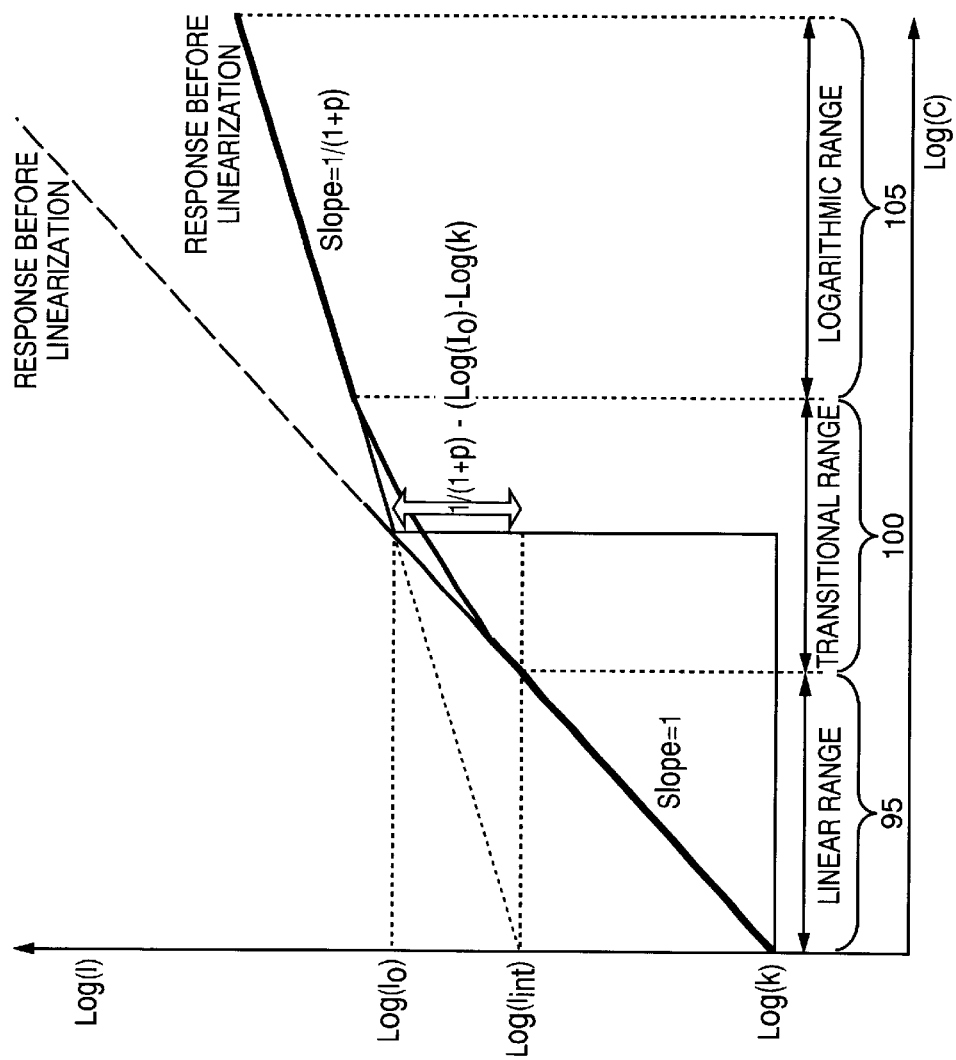
FIG. 3 shows a log-log plot of the IMS response factor before and after linearization.

FIG. 3 is a Log-Log plot of the IMS response. FIG. 3 depicts the linear response range 95, the transitional response range 100, and the logarithmic response range 105 both before and after linearization.

Equation 1 describes the IMS linearizing function.

$$I_{lin}=I(1+I/I_o)^p \quad (1)$$

where:
  $I_{lin}$ is the linearized output current,
  $I$ is the output current to be linearized,
  $I_o$ is the virtual output current to which the linear and the logarithmic ranges extrapolate in a logarithmic plot, as shown in FIG. 3, and
  p is the linearizing power such that the slope of the logarithmic range is $1/(1+p)$. Note that p=0 for a linear relation and p=1 for a square root relation.

Figure 4:
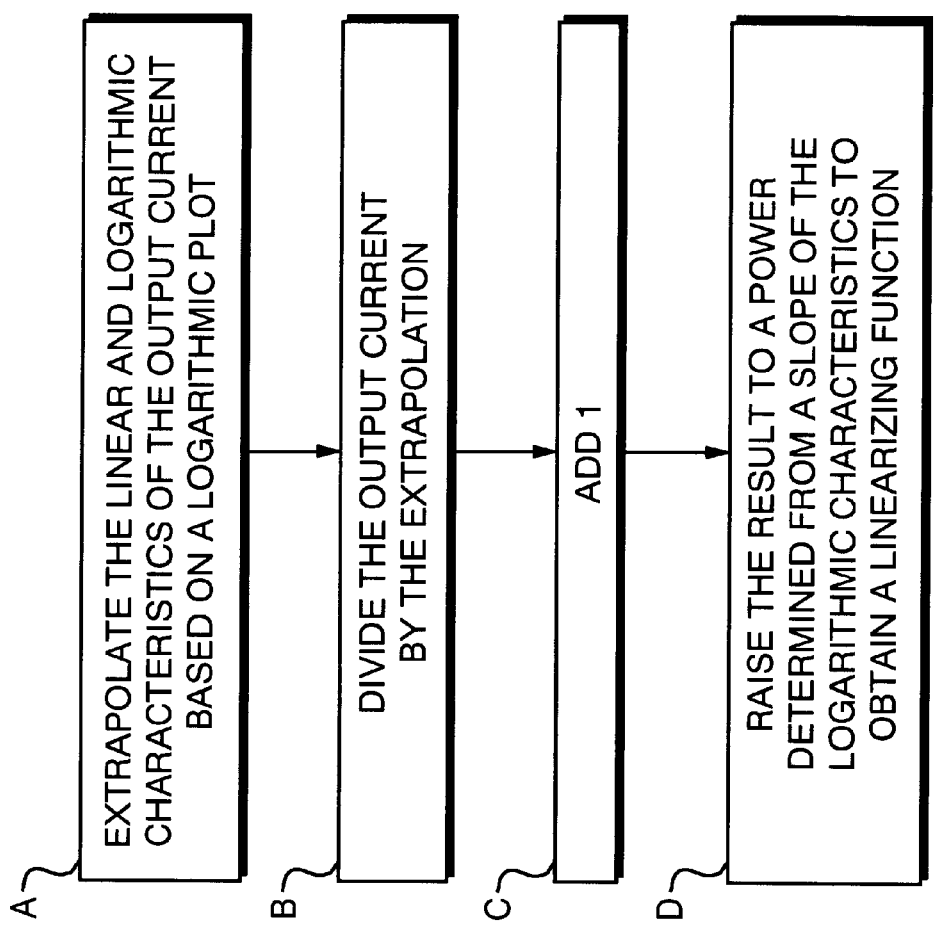
FIG. 4 shows steps for determining a linearizing function in accordance with the teachings of this invention.

FIG. 4 shows the steps for determining the linearizing function. In step A, the linear and logarithmic characteristics of the output current are extrapolated based on a logarithmic plot. In step B, the output current is divided by the extrapolation. In step C, 1 is added, and in step D, the result is raised to a power determined from a slope of the logarithmic characteristics to obtain the linearizing function.

Figure 5:
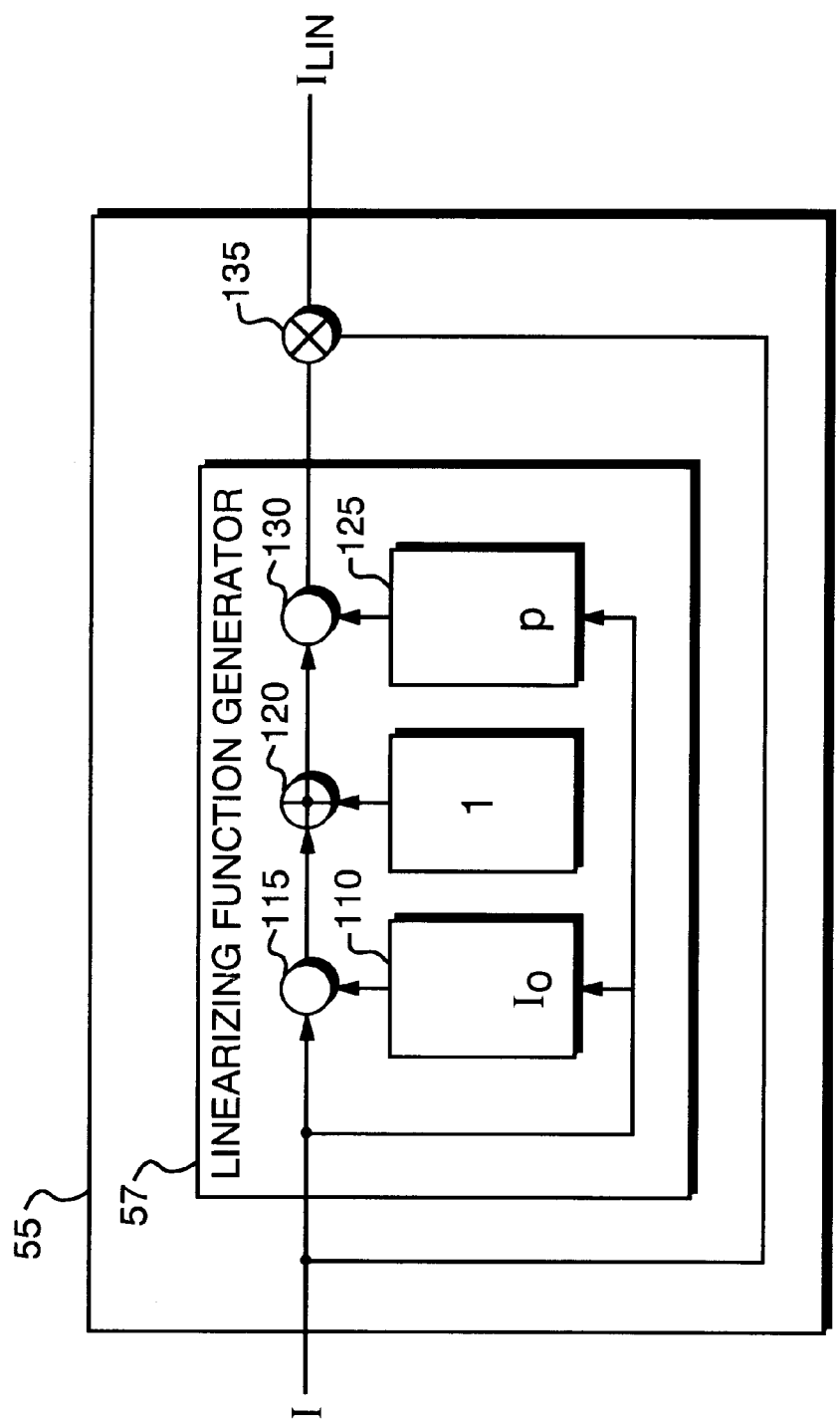
FIG. 5 shows a block diagram of circuitry for linearizing the output of an ion mobility spectrometer in accordance with the teachings of this invention.

FIG. 5 shows a block diagram of a preferred embodiment of the circuitry 55. The output of the ion sensor 55 is fed into a linearizing function generator 57. The linear and logarithmic characteristics of the output current are extrapolated based on a logarithmic plot in block 110 and the output current is divided by the extrapolation in junction 115. A 1 is added in junction 120. A power is determined from a slope of the logarithmic characteristics in block 125 and the result of junction 120 is raised to that power in junction 130. At junction 135, the result of the linearizing function generator is multiplied by the output current to obtain a linearized current.

The derivation of the linearization function is shown in the following proof:
  a. The Linear Range:
  In the linear response range of the IMS, the response factor may be expressed as:

$$I=kC \quad (2)$$

Where k is the response factor in the linear range, and C is the analyte concentration. Taking the log of both sides of Equation 2, $$\text{Log}(I)=\log(k)+\log(C) \quad (3)$$

In the linear range I<<Io, Equation 1 becomes:

$$I_{lin}=I \quad (4)$$

Therefore, combining equation 2 and equation 4, one obtains:

$$I_{lin}=kC \quad (5)$$

It can be seen therefore that the linearizing function operates to preserve the linear range.
  b. The Logarithmic Range:
  In the logarithmic range where I>>Io, equation (1) becomes:

$$I_{lin}=I^{(1+p)}/I_o^p \quad (6)$$

Taking the log of both sides, $$\text{Log}(I_{lin})=(1+p)\text{Log}(I)-p\text{Log}(I_o) \quad (7)$$

which can be re-written as:

$$\text{Log}(I)=1/(1+p)\text{Log}(I_{lin})+p/(1+p)\text{Log}(I_o) \quad (8)$$

Referring now to FIG. 2, the logarithmic range may be defined by the following expression:

$$\text{Log}(I)=\text{Log}(I_{int})+1/(1+p)\text{Log}(C) \quad (9)$$

In FIG. 2 it can be seen that:

$$\text{Log}(I_{int})-\text{Log}(k)=\{\text{Log}(I_o)-\text{Log}(k)\}-1/(1+p)\{\text{Log}(I_o)-\text{Log}(k)\}$$

which can be rewritten as:

$$\text{Log}(I_{int})=p/(1+p)\text{Log}(I_o)+1/(1+p)\text{Log}(k) \quad (10)$$

Substituting from equation (10) into equation (9), one obtains:

$$\mathrm{Log}(I)=p/(1+p)\mathrm{Log}(I_o)+1/(1+p)\mathrm{Log}(k)+1/(1+p)\mathrm{Log}(C)$$

which can be re-arranged as:

$$\mathrm{Log}(I)=1/(1+p)\mathrm{Log}(kC)+p/(1+p)\mathrm{Log}(I_o) \quad (11)$$

By comparing equation 11 to equation 8 it can be seen that $\mathrm{Log}(I_{lin})$ must be equal to $\mathrm{Log}(kC)$. Hence:

$$I_{lin}=kC \quad (12)$$

Equation 12 shows clearly that the output of the linearizing function in the logarithmic range is the same as its output in the linear range.

C. The Transitional Range:

Because this function provides a smooth transition from the linear to the logarithmic range, the transitional range will also be linearized.

As described above, the linearizing function can be incorporated into the design of the IMS and its operation can be made transparent to the user. The user can be relieved of preparing his own calibration curves and from the sample dilution process required to operate in the linear response range of the IMS. Because the function operates on the output current of the IMS detector 10, the function provides a quantitatively accurate and precise linearized response.

While the linearization function has been disclosed in the context of a data processor as the circuitry 55, it should be understood that the implementation of the linearization function is not limited to only a data processor embodiment using a computer program, such as firmware (e.g., program code in a ROM, PROM, EPROM, or the like). For example, all or part of the linearizing process could be carried out by dedicated circuitry, such as analog operational amplifiers and similar components.

While the invention has been particularly shown and described with respect to preferred embodiments thereof, it will be understood by those skilled in the art that changes in form and details may be made therein without departing from its scope and spirit.

What is claimed is:

1. An ion mobility spectrometer comprising:
    a sensor for detecting ions, said sensor having an output with linear, non-linear, and logarithmic characteristics; and
    circuitry coupled to said sensor for linearizing said output such that said non-linear and logarithmic characteristics are linearized while preserving said linear characteristics.

2. The ion mobility spectrometer of claim 1, wherein said circuitry operates to linearize said output by multiplying said output by a first function, said first function being determined from a second function by extrapolating linear and logarithmic characteristics based on a logarithmic plot, dividing the output current by the extrapolation, adding 1, and raising the result to a power determined from a slope of said logarithmic characteristics to obtain a linearizing function.

3. The ion mobility spectrometer of claim 2, wherein said circuitry operates to yield one continuous linear plot in conformance with a fundamental gain of said ion sensor.

4. The ion mobility spectrometer of claim 1, wherein said ion generator further comprises a radioactive material selected from one of the group of one of the group of tritium, Ni, and Am.

5. The ion mobility spectrometer of claim 1, wherein said ion generator further comprises a photo-ionization source.

6. An ion mobility spectrometer comprising:
    a sample input port;
    an ion generator;
    an ionization chamber coupled to said sample input port and said ion generator for receiving and ionizing samples;
    an ion gate for causing said ionized samples to travel in a direction;
    a drift region for receiving said directed ionized samples and for subjecting said ionized samples to an electric potential, whereby said ionized samples separate according to their electric charge and mass;
    a sensor for detecting said separated ions, said sensor having an output with linear, non-linear, and logarithmic characteristics; and
    circuitry coupled to said sensor for linearizing said output such that said non-linear and logarithmic characteristics are linearized while preserving said linear characteristics.

7. A method of linearizing an output of an ion mobility spectrometer comprising the steps of:
    detecting sample ions with a sensor having an output with linear, non-linear, and logarithmic response characteristics; and
    linearizing said output such that said non-linear and logarithmic response characteristics are linearized while preserving said linear response characteristics.

8. The method of claim 7 wherein said step of linearizing further comprises the step of:
    multiplying said output by a first function, said first function being determined from a second function by extrapolating linear and logarithmic characteristics based on a logarithmic plot, dividing the output current by the extrapolation, adding 1, and raising the result to a power determined from a slope of said logarithmic characteristics to obtain a linearizing function.

9. The method of claim 8, wherein said step of linearizing further comprises yielding one continuous linear plot in conformance with a fundamental gain of said sensor.

10. The method of claim 7, wherein said step of ionizing is performed utilizing a radioactive material selected from one of the group of one of the group of tritium, Ni, and Am.

11. The method of claim 7, wherein said step of ionizing is performed utilizing a photo-ionization source.

12. A method of linearizing an output of an ion mobility spectrometer comprising the steps of:
    ionizing a sample to produce sample ions;
    causing said sample ions to travel in a direction;
    subjecting said sample ions to an electric field causing individual ones of said sample ions to separate according to their mass and charge;
    detecting said individual ones of said sample ions with a sensor having an output with linear, non-linear, and logarithmic response characteristics; and
    linearizing said output such that said non-linear and logarithmic response characteristics are linearized while preserving said linear response characteristics.

* * * * *